United States Patent [19]

Kanaoka

[11] 4,097,488

[45] Jun. 27, 1978

[54] N-(3-FLUORANTHYL)MALEIMIDE; A FLUORESCENT REAGENT FOR THE STUDIES OF THIOL COMPOUNDS

[75] Inventor: Yuichi Kanaoka, Sapporo, Japan

[73] Assignee: Teika Seiyaku Kabushiki Kaisha, Toyama, Japan

[21] Appl. No.: 771,634

[22] Filed: Feb. 24, 1977

[30] Foreign Application Priority Data

Apr. 6, 1976 Japan .................................. 51-38485

[51] Int. Cl.$^2$ ........................................... C07D 207/30

[52] U.S. Cl. ....................... 260/326.5 C; 260/326.5 S
[58] Field of Search ............... 260/326.5 FM, 326.5 C

*Primary Examiner*—Jose Tovar
*Attorney, Agent, or Firm*—Scrivener, Parker, Scrivener & Clarke

[57] ABSTRACT

This invention relates to N-(3-fluoranthyl)maleimide which is reactive with thiol compounds forming fluorescent products, and is useful in the fields of biochemical research.

1 Claim, No Drawings

N-(3-FLUORANTHYL)MALEIMIDE; A FLUORESCENT REAGENT FOR THE STUDIES OF THIOL COMPOUNDS

DETAILED DESCRIPTION OF THE INVENTION

This fluorescent reagent can be utilized to study the physico-chemical characteristics of bio-macromolecules such as proteins and nucleic acids in their micro-environments, and to measure kinetics in intra-molecular mutual action. The basic idea of the fluorescent reagent is based on the fact that the fluorescent spectra are generally sensitive to changes of the micro-environments, and shows explicit and specific fluorescent characteristics. The emmision properties of the fluorescence can be characterized from various aspects such as spectral distribution, life times, quantum yield, degree of polarization and so on.

The inventor has so far developed several unique fluorescent reagents of maleimide-type for the studies of the thiol compounds through a series of systematic research. All of these maleimide-type reagents have the special characteristics that they do not fluoresce by themselves, but the adducts formed by easily reacting with thiol compounds in bio-macromolecules do fluoresce. However, the life times of the fluorescence limited from the adducts of the maleimide-type fluorescence reagents and thiol compounds are in most cases less than 10 nsec which are too short for usual biological research application.

The inventor has now created, through the screening of numerous aromatic compounds, the biologically useful fluorescent reagent, N-(3-fluoranthyl)maleimide, that forms the adducts having conveniently measurable fluorescent life times. This substance and thiol compounds react to form adducts whose fluorescent life times are approximately 20 nsec and this value is suited for various biological studies.

If the lifetime of a molecule at fluorescent state is sufficiently long, a variety of interactions can take place within the lifetime: molecular not rotation, orientational alteration, molecular deformation, photochemical reaction, solvent-interaction, energy transfer, and forming of excitation complex with other molecules. Thus, the said invention shall provide new means for the development of such fields of research when its reactivity to thiol radicals and its fluorescent characteristics are utilized.

An example of the production of the invented substance, N-(3-fluoranthyl)maleimide is shown below.

When 540 mg of maleic acid anhydride is dissolved in 30 ml of benzene and stirred, and then a solution of 1,085 mg of 3-amino-fluoranthene in 15 ml of benzene is added little by little, yellow crystal is immediately educed. After completing the reaction by continuing to stirr for 3 hours at room temperature, the filtrated crystal is washed with benzene and dried. Thus, 1,520 mg of N-(3-fluoranthyl)maleamine acid (yellow powder, melting point, 198° - 200° C) is produced (yield: 96%).

Then a mixture of 315 mg of this maleamine acid, 1,500 mg of acetic anhydide and ;B 30 mg of anhydrous sodium acetate is heated at 100° C in oil-bath for 40 minutes. After cooling, the reacted mixture is poured in ice water, and then neutralized by adding sodium bicarbonate powder, extracted with dichloromethane solution. After washing with saturated aqueous solution of sodium bicarbonate, saturated aqueous solution of sodium chloride, and water successively, the extracted solution is dried with dehydrating sodium sulfate, solvent removed by distillation, and the residue is recrystallized with benzene. Thus, N-(3-fluoranthyl)maleimide (yellow, neddle-like crystal, melting point: 185° - 186° C, 226 mg) is obtained (yield: 76%).

The above mentioned N-(3-fluoranthyl)maleimide has composition $C_{20}H_{11}NO_{20}$, molecular weight: 297.286, and its elementaly analysis values are as follows.

|  | C | H | N |
|---|---|---|---|
| Theoretical value | 80.80 | 3.72 | 4.70 |
| Measured value | 80.74 | 3.65 | 4.64 |

An example of this structure is shown in the following chemical formula;

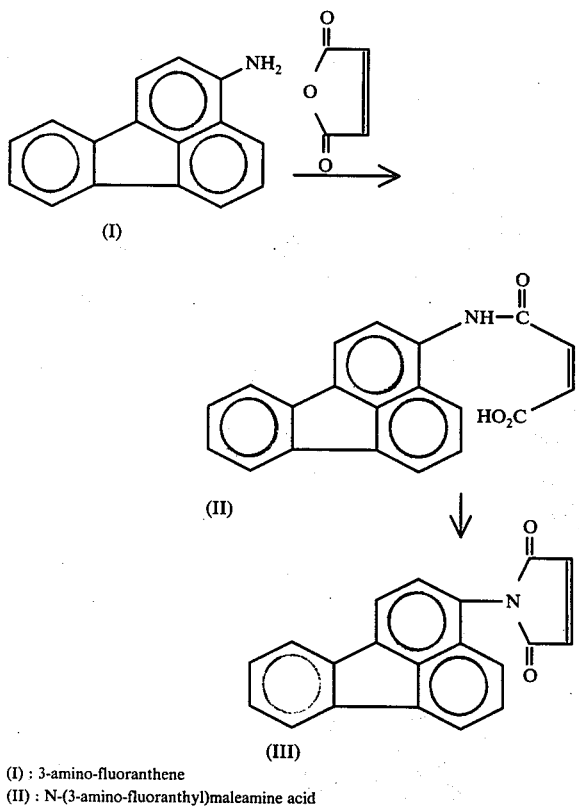

(I) : 3-amino-fluoranthene
(II) : N-(3-amino-fluoranthyl)maleamine acid
(III) : N-(3-amino-fluoranthyl)maleimide The reaction between this invented substance, N-(3-fluoranthyl) maleimide and thiol compounds proceeds as follows:

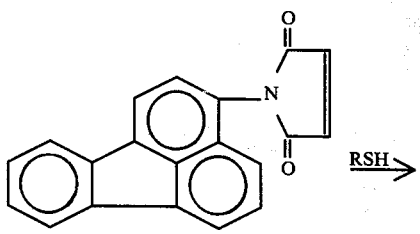

-continued

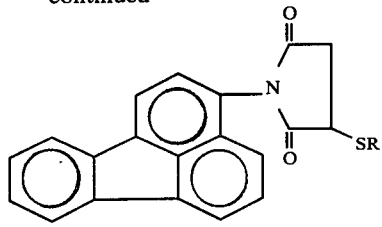

Namely, $10^{-5}$ mol/ml of the invented N-(3-fluoranthyl)maleimide dissolved in 1 ml of acetone is allowed to react overnight at 4° C with added L-cysteine hydrochloride 1 mg as an example of substance containing a thiol group, and the fluorescence is measured. The intensity of fluorescence is in direct proportion to the concentration of L-cysteine hydrochloride solutions ranging from 0.03 γ/ml to 0.5 γ/ml.

| Concentration of L-cysteine hydrochloride γ/ml | Relative fluorescence intensity |
|---|---|
| 0.034 | 0.081 |
| 0.102 | 0.225 |
| 0.270 | 0.530 |
| 0.340 | 0.765 |
| 0.510 | 0.957 |

Also, for relative fluorescence intensity, a solution of quinine sulfate (0.2 γ/ml) in 0.1 N sulfuric acid was used as standard.

When 45 mg of egg-albumin is dissolved into 20 ml of 0.1 N phosphate buffer (pH 7.0) and allowed to react at 4° C overnight with 1.6 ml of $5 - 10^{-3}$M 1,2-dimethoxyethane solution of N-(3-fluoranthyl)maleimide, the ultraviolet spectrum and the amino acid analyses show that 0.3 mol of N-(3-fluoranthyl)maleimide is incorporated per 1 mol of egg-albumin.

| Thiol compound | excitation wave length | max. wave length of fluorescence | quantum yield |
|---|---|---|---|
| L-cysteine hydrochloride | 362 nm | 462 nm | 0.25 |
| Egg-alubmin | 362 nm | 462 nm | 0.16 |

Addition products formed from the invented N-(3-fluoranthyl) maleimide and thiol compound show fluorescence spectra which have medium life time around 20 nsec.

Therefore, the above mentioned N-(3-fluoranthyl)-maleimide provides a reagent as a new dynamic probe for obtaining information on the time-dependent processes of various biological systems including biopolymers, membranes and other complex systems.

What is claimed is:
1. A compound of the formula:

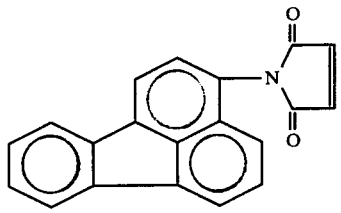

* * * * *